United States Patent
Lalanne-Magne et al.

(10) Patent No.: US 6,323,362 B1
(45) Date of Patent: Nov. 27, 2001

(54) CONTINUOUS PROCESS FOR PRODUCING ESTERS

(75) Inventors: Philippe Lalanne-Magne, Saint Mitre les Remparts; Bruno Grenouiller, Martigues; Daniel Brun-Buisson, Istres, all of (FR)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/556,969

(22) Filed: Apr. 24, 2000

Related U.S. Application Data (63) Continuation of application No. 08/990,835, filed on Dec. 15, 1997, now abandoned.

(30) Foreign Application Priority Data

Dec. 17, 1996 (FR) .................................................. 96 15808

(51) Int. Cl.⁷ .................................................. C07C 67/02
(52) U.S. Cl. .................................................. 560/234
(58) Field of Search .................................................. 560/234

(56) References Cited

U.S. PATENT DOCUMENTS

| | | | |
|---|---|---|---|
| 1,425,624 | * 8/1922 | Backhaus | 560/234 |
| 3,700,726 | 10/1972 | Johnson, Jr. et al. | 260/491 |
| 4,370,491 | 1/1983 | Bott et al. | 560/234 |
| 4,458,088 | * 7/1984 | Hardman et al. | 560/96 |
| 4,559,180 | * 12/1985 | Green | 560/234 |
| 4,960,927 | * 10/1990 | Canonge et al. | 560/234 |
| 5,350,879 | * 9/1994 | Engel et al. | 560/234 |
| 5,405,992 | * 4/1995 | Funk et al. | 560/234 |

FOREIGN PATENT DOCUMENTS 2 017 083 A    10/1979 (GB) .

\* cited by examiner

Primary Examiner—Paul J. Killos
Assistant Examiner—Taylor V Oh
(74) Attorney, Agent, or Firm—Finnegan, Henderson, Farabow, Garrett and Dunner, L.L.P.

(57) ABSTRACT

A process for the continuous and simultaneous manufacture of at least two different acetates by at least two simultaneous transesterification reactions comprising continuously bringing into contact in the presence of a catalyst in a reaction zone: (i) an acetate of the formula $CH_3COOR$ in which R is an alkyl radical, with (ii) at least two alcohols of formulae $R^1OH$ and $R^2OH$ in which $R^1$ and $R^2$, are different, and are alkyl radicals with a linear or branched chain, or radicals of formula $R^3(OCH_2CR^4R^5)_m$— in which $R^3$ is an alkyl radical, $R^4$ and $R^5$, being identical or different, are a hydrogen atom or an alkyl radical, and m is an integer of from 1 to 4 to form a reaction mixture having a homogeneous liquid phase and produce in the reaction zone by at least two simultaneous transesterification reactions of (i) with (ii) at least two acetates of formulae $CH_3COOR^1$ and $CH_3COOR^2$ and continuously drawing off from the reaction zone the at least two acetates and continuously separating the at least two acetates from each other by at least twice successively distilling the reaction mixture present in the reaction zone.

13 Claims, 4 Drawing Sheets

CONTINUOUS PROCESS FOR PRODUCING ESTERS

This is a continuation of application Ser. No. 08/990,835, filed Dec. 15, 1997, now abandoned incorporated herein by reference.

BACKGROUND OF THE INVENTION

The present invention relates to a process for continuous manufacture of esters, or in particular of acetates, by a catalytic transesterification reaction in a homogeneous liquid phase.

British patent application GB-2 017 083 describes a process for the manufacture of ethylmonoglycol ether acetate by a catalytic transesterification reaction using ethyl acetate and ethylmonoglycol ether. The reaction is carried out in a heterogeneous phase in the presence of a catalyst consisting of a solid ion exchange resin at a relatively low temperature, lower than 100° C.

U.S. Pat. No. 3,700,726 discloses a process for the manufacture of (poly)ethylene glycol ether acetate by a catalytic transesterification reaction using an alkyl acetate with a (poly)ethylene glycol ether in the presence of a catalyst chosen from metal alcoholates. During the reaction only one alcohol is used, which is a (poly)ethylene glycol ether.

U.S. Pat. No. 4,370,491 and French patent FR-2 611 704 disclose processes for the manufacture of acetate by a catalytic transesterification reaction using an acetate and an alcohol in the presence of a catalyst chosen from metal alcoholates.

It has been noticed that an industrial unit continuously manufacturing esters, or in particular acetates, according to the processes as described above must be stopped for several days each time that the type of ester to be manufactured is changed. It has been observed that, in general, such an industrial unit can thus be stopped for one or two months a year, which corresponds to considerable losses of output.

Furthermore, search is continuing for processes which enable esters, or in particular acetates, to be manufactured with a high degree of purity, that is to say containing very few by-products.

SUMMARY OF THE INVENTION

A very economical process has just been found, making it possible to manufacture continuously and simultaneously at least two, preferably two, esters, or in particular two acetates, with high degrees of purity.

The subject-matter of the present invention is therefore a process for the manufacture of esters, or in particular of acetates, by transesterification reaction in a homogeneous liquid phase, characterized in that at least two, preferably two, esters, or in particular acetates, are manufactured continuously and simultaneously by at least two, preferably two, simultaneous transesterification reactions in a homogeneous liquid phase, which are carried out in a reaction zone (RZ), (a) by continuously introducing into the said zone (1) a catalyst, (2) an organic ester, in particular an ester of a carboxylic, in particular aromatic or preferably aliphatic acid, for example from $C_1$ to $C_{12}$, preferably from $C_1$ to $C_6$, for example an acetate, and (3) simultaneously at least two, preferably two, different alcohols in particular from $C_1$ to $C_{16}$, preferably from $C_1$ to $C_{12}$, it being possible for at least one of the two alcohols to be chosen from primary or secondary alcohols and the other alcohol from secondary or tertiary alcohols, it being possible for the difference in boiling temperature of at least the two alcohols at atmospheric pressure to be furthermore advantageously from 10 to 60° C., preferably from 20 to 50° C., and (b) by continuously drawing off from the said zone at least the two, preferably the two, esters manufactured, or in particular the acetates manufactured, and by separating them continuously by means of at least two, preferably two, successive distillations of the reaction mixture present in the said zone.

The process is very particularly suitable for continuously and simultaneously manufacturing at least two, preferably two, acetates (IV) and (V), by at least two, preferably two, simultaneous transesterification reactions in a homogeneous liquid phase, which are carried out in a reaction zone (RZ), by bringing into contact in the presence of a catalyst:

(i) an acetate of formula (1)

in which R denotes an alkyl radical, in particular from $C_1$ to $C_4$ with

(ii) at least two, preferably two, alcohols of formulae (II)

and (III)

in which $R^1$ and $R^2$, being different, denote alkyl radicals with a linear or branched chain, in particular from $C_4$ to $C_{12}$, or radicals of formula in which $R^3$ denotes an alkyl radical, in particular from $C_1$ to $C_6$, $R^4$ and $R^5$, being identical or different, denote a hydrogen atom or an alkyl radical in particular from $C_1$ to $C_4$, preferably $C_1$ or $C_2$, for example methyl, and m is an integer ranging from 1 to 4, preferably equal to 1 or 2, the products resulting from these reactions including at least the two, preferably the two, desired acetates, of formulae (IV)

and (V)

in which formulae $R^1$ and $R^2$ have the same definitions as above.

The process of the present invention may advantageously include the following operations:

(a) at least the two, preferably the two, simultaneous transesterification reactions are simultaneously carried out continuously in the reaction zone (RZ), the products resulting from these reactions being at least the two, preferably the two, desired esters, or in particular acetates, in particular of formulae (IV) and (V), and an alcohol, in particular of formula $$ROH \quad (VI)$$

in which R has the same definition as above, the products brought into contact in the reaction zone (RZ) forming a reaction mixture with the products resulting from these reactions, (b) a distillation (D1) of the reaction mixture is carried out continuously at a pressure which is substantially identical with that existing in the reaction zone (RZ), by continuously separating a light fraction containing at least one azeotropic mixture (M1) formed of the initial ester (used), or in particular the acetate (I), with the alcohol formed, in particular of type (VI), from a heavy fraction containing at least the two, preferably the two, esters manufactured, or in particular acetates (IV) and (V), (c) a distillation (D2) of the light fraction from (D1) is carried out continuously at a pressure which differs from that existing in (D1), so as to separate off continuously a portion of the alcohol formed in particular of type (VI), and (d) at least two, preferably two, successive distillations (D3) and (D4) of the heavy fraction from (D1) are carried out continuously, so as to separate off continuously at least the two, preferably the two, esters manufactured or in particular acetates (IV) and (V).

DETAILED DESCRIPTION OF THE INVENTION

The process of the present invention relates to the continuous and simultaneous manufacture of two or more esters, or in particular acetates. If the number of esters, or in particular of acetates, to be manufactured is n, then it is recommended that according to the present invention the initial ester, or in particular the acetate (I), will be used in the reaction zone (RZ) with n different alcohols, in particular of formulae which are identical with those given above for the alcohols (II) and (III). In this case the reaction mixture will include the products used in (RZ) and the products resulting from the n simultaneous transesterification reactions. The process will also be capable of including the continuous distillation operations similar to those of the distillation (D1) and (D2) described above, as well as a continuous distillation operation comprising at least n successive distillations from (D3) to (Dn+2), similar to (D3) and (D4) described above, enabling the desired n esters, or in particular acetates, to be separated and isolated.

The process of the present invention can operate for continuously and simultaneously manufacturing more than two esters, or in particular acetates, for example three esters, or in particular acetates, and is very particularly suitable for continuously and simultaneously manufacturing two acetates. The remainder of the description will concern the manufacture in particular of two acetates, but is easily adaptable to allow the continuous and simultaneous manufacture of more than two esters, or in particular acetates, to be carried out.

In the reaction zone (RZ) there are continuously and simultaneously carried out at least two, preferably two, transesterification reactions which can be written according to the following equilibrium reactions $(A_1)$ and $(A_2)$:

in which R, $R^1$ and $R^2$ have the same definitions as above. There will be n equilibrium reactions of this type for manufacturing n esters, or in particular acetates, it being possible for the nth equation (An) to be written as follows:

in which the alcohol $R''OH$ is different from the other alcohols used, with $R''$ having a definition that is identical with that given above for $R^1$ and $R^2$, and the nth ester, or in particular acetate, to be manufactured simultaneously with the other (n−1) esters, or in particular acetates, can correspond to the formula $CH_3COOR''$.

The acetate (I) used in the simultaneous transesterification reactions may correspond to the formula $CH_3COOR$ in which R denotes an alkyl radical, in particular from $C_1$ to $C_4$, for example the methyl, ethyl, n-propyl or n-butyl radical, preferably the ethyl radical.

Also, at least two, preferably two, different alcohols of formulae $R^1OH$ (II) and $R^2OH$ (III) are used, in which $R^1$ and $R^2$, being different, denote alkyl radicals with a linear or branched chain, in particular from $C_4$ to $C_{12}$, preferably $C_6$ to $C_{10}$, for example $C_8$. In particular, primary or secondary or tertiary alcohols, for example 1-octanol and/or 2-ethyl-1-hexanol, may be employed.

The alcohols (II) and (III) which are used may also be chosen from glycol ethers, also called mono- or polyalkylene glycol ethers, corresponding to the formula $$R^3(OCH_2CR^4R^5)_mOH \quad (VII)$$

in which $R^3$ denotes an alkyl radical, in particular from $C_1$ to $C_6$, preferably from $C_1$ to $C_5$, in particular from $C_1$ to $C_4$, such as the methyl, ethyl or n-butyl radical, $R^4$ and $R^5$, being identical or different, denote a hydrogen atom or an alkyl radical, in particular from $C_1$ to $C_4$, preferably $C_1$ or $C_2$, for example methyl, and m is an integer ranging from 1 to 4, preferably equal to 1 or 2.

The process of the present invention is suitable in particular when at least two, preferably two, alcohols, in particular of type (II) and (III), are used, one chosen from primary or secondary alcohols, the other from secondary or tertiary alcohols. It is very particularly suitable when at least the two, preferably the two, alcohols (II) and (III) are chosen from the glycol ethers corresponding to the formula (VII) cited above. It is suitable preferably when at least the two, in particular the two, alcohols (II) and (III) are glycol ethers, one of the glycol ethers being chosen from the mono- or polyethylene glycol ethers corresponding to the formula (VII) in which $R^4$ and $R^5$ denote a hydrogen atom, that is to say correspond to the formula $$R^3(OCH_2CH_2)_mOH \qquad (VIII)$$

and the other glycol ether being chosen from the mono- or polypropylene glycol ethers corresponding to the formula (VII) in which $R^4$ denotes a hydrogen atom and $R^5$ a methyl radical, that is to say corresponding to the formula $$R^3(OCH_2CHCH_3)_mOH \qquad (IX)$$

in which formula $R^3$ and m have the same definitions as above.

The process is also well suited when at least the two, preferably the two, alcohols (II) and (III) are chosen from mono- or polyethylene glycol ethers of formula (VIII) or from mono- or polypropylene glycol ethers of formula (IX).

It has been noticed that the process of the present invention operates particularly well in particular when at least the two, preferably the two, alcohols, in particular of types (II) and (III), used have boiling points at atmospheric pressure which are such that their difference is from 10 to 60° C., preferably from 20 to 50° C.

The transesterification reactions are carried out in the presence of a catalyst which is soluble in the reaction mixture. The catalyst may be chosen from metal alcoholates, in particular alcoholates of metals belonging to groups I to IV of the Periodic Classification of the elements, for example sodium, potassium, aluminium or titanium. It is preferred to employ titanium alcoholates such as tetraethyl titanate.

It has surprisingly been observed that the process for continuous and simultaneous manufacture of at least two, preferably two, esters, or in particular acetates, according to the present invention, results in esters, or in particular acetates, of very high purity being obtained, without forming substantial quantities of by-products obtained, for example, by other reactions with impurities brought in by the reactants. This is all the more surprising since primary and secondary or tertiary alcohols, in particular of types (II) and (III), are simultaneously used, for example one of the alcohols (II) and (III) being chosen from mono- or polyethylene glycol ethers of formula (VIII) and the other chosen from mono- or polypropylene glycol ethers of formula (IX). It is also surprising that in the process of the present invention one of the simultaneous transesterification reactions is not favoured in relation to the other reactions. As a result of this also at least the two, preferably the two, esters manufactured, or in particular acetates (IV) and (V), are thus obtained and drawn off in molar proportions that are substantially identical with the molar proportions of at least the two, preferably the two, alcohols introduced, in particular of (II) and (III) type, molar proportions which can thus vary within a range extending from 0.01 to 100, for example from 0.1 to 10, preferably from 0.2 to 5.

The simultaneous transesterification reactions are carried out in particular in a reaction zone (RZ) where a temperature is maintained which can range from 100 to 200° C., preferably from 110 to 190° C., for example from 120 to 180° C., at an absolute pressure P1 ranging from 0.1 to 1 MPa, preferably from 0.1 to 0.5 MPa. The initial ester, or in particular the acetate (I), introduced can be advantageously reacted in a molar quantity that is substantially identical with the total molar quantity of the alcohols used, in particular of types (II) and (III).

The reaction mixture thus prepared in the reaction zone (RZ) can be advantageously subjected continuously to a distillation (D1) at a pressure that is substantially identical with that, P1 prevailing in the reaction zone. In particular, the reaction zone can be directly surmounted by a distillation (D1) column. The latter may be designed to separate off at the top a light fraction containing an azeotropic mixture (M1) consisting of the initial ester, or in particular the acetate (I), and of the alcohol formed, in particular of (VI) type. In practice the distillation (D1) column can be a tray- or packed column and can have a number of theoretical plates ranging approximately from 10 to 30.

The light fraction from the distillation (D1) containing in particular the azeotropic mixture (M1) can be advantageously continuously subjected to a distillation (D2) operating at an absolute pressure, P2, which differs from that existing in the distillation (D1) and in particular in the reaction zone (RZ). The absolute pressure, P2, is preferably lower than the pressure existing in (D1), and in particular lower than P1, in order to facilitate the separation of a proportion of the alcohol formed, in particular of (VI) type. The absolute pressure, P2, may be in particular lower than atmospheric pressure and more particularly equal to a value ranging from 0.005 to 0.1 MPa, preferably from 0.01 to 0.09 MPa. The distillation (D2) may be carried out in practice in at least one try- or packed distillation column which has, for example, a number of theoretical plates ranging approximately from 10 to 30. The distillation (D2) is generally designed to separate, for example, at the tail end, a portion of the alcohol formed, in particular of (VI) type, which is then isolated and recovered and to form, for example, at the top, a new azeotropic mixture (M2) consisting of the initial ester, or in particular the acetate (I), and the alcohol formed, in particular of (VI) type, in a content that is lower than that of alcohol formed, in particular of (VI) type, in the mixture (M1).

In a preferred alternative form of the process according to the present invention the new azeotropic mixture (M2) resulting from the distillation (D2) and in particular from the separation and from the removal of at least a portion of the alcohol formed, in particular of (VI) type, is at least partly returned continuously into the reaction zone (RZ) and/or into the distillation (D1), preferably into the distillation (D1). This makes it possible to improve considerably the yield of the process in respect of the esters, or in particular acetates, of the types (IV) and (V) which are manufactured.

The heavy fraction from the distillation (D1) may be advantageously continuously subjected to at least two, preferably two, successive distillations (D3) and (D4). Thus, for example, the heavy fraction from (D1) is continuously subjected firstly to a distillation (D3) where in particular the ester, or in particular the acetate, which is the lightest is separated from at least the two, preferably the two, esters, and in particular acetates, (IV) and (V) which are manufactured, it being possible for the top fraction from (D3) to be advantageously at least partly returned continuously into the reaction zone (RZ) and/or into the distillation (D1), and the tail fraction from (D3) continuously feeding the distillation (D4). In practice, in the distillation (D4), the ester, or in particular the acetate, which is the heaviest is separated from at least the two, preferably the two, esters, or in particular acetates, (IV) and (V) which are manufactured, it being possible for the top and tail fractions to be advantageously at least party returned continuously into the reaction zone (RZ) and/or into the distillation (D1). The catalyst may be in particular recovered in the tail fraction (D4) and thus returned towards the reaction zone (RZ). Each of the distillations (D3) and (D4) may be carried out in one or preferably in two tray- or packed distillation columns which have a number of theoretical plates ranging approximately from 3 to 30. These distillations are preferably carried out at a pressure which is lower than atmospheric pressure, ranging from 0.005 to 0.1 MPa, preferably from 0.01 to 0.09 MPa.

The tail fraction from (D4), containing in particular the catalyst, may be returned into the reaction zone (RZ) at a point which is different from or preferably identical with that of the introduction of the fresh catalyst. In practice a small portion of this fraction, containing in particular the catalyst in a partially deactivated form, may be continuously or intermittently removed by a purge. As a result, in order to maintain a constant catalyst concentration in the reaction mixture, an additional quantity of fresh catalyst, equivalent to that of catalyst removed by purging, is then introduced continuously or intermittently into the reaction zone (RZ). The catalyst concentration in the reaction mixture may be such that the molar ratio of the quantity of catalyst to the sum of the quantities of alcohols used, in particular of types (II) and (III), is from $5\times10^{-4}$ to $5\times10^{-2}$, preferably from $10^{-3}$ to $10^{-2}$.

The fresh reactants consisting of the initial ester, or in particular the acetate (I), and at least the two, preferably the two, alcohols used, in particular of types (II) and (III), as well as the catalyst, may be introduced into the reaction mixture in various ways. They may be all introduced continuously and simultaneously either directly into the reaction zone (RZ) or into the distillation (D1). One of the preferred methods consists in introducing the catalyst separately from the fresh reactants, directly into the reaction zone (RZ), as described in French patent application FR-2 611 704. The fresh reactants, for their part, may then be continuously introduced simultaneously or separately into the distillation (D1). They may be continuously introduced simultaneously and as a mixture with the new azeotropic mixture (M2) resulting from the distillation (D2), at least partly continuously returned towards the distillation (D1). If, on the contrary, the reactants are introduced separately from one another, their points of introduction successively from the bottom upwards into the distillation (D1) column are those corresponding respectively to the initial ester, or in particular the acetate (I), then to the lightest alcohol of the alcohols used, in particular of types (II) and (III), to the heaviest alcohol of the alcohols used, in particular of types (II) and (III), and optionally the new azeotropic mixture (M2) returned at least partly from the distillation (D2).

Another alternative form of introduction of the reactants into the distillation (D1) may consist in introducing all the fresh reactants as well as the new azeotropic measure (M2) at least partly returned from the distillation (D2) via two separate entry lines into the distillation (D1):

a first entry line brings a portion of the initial ester, or in particular the acetate (I), and of the mixture (M2) and all of the lightest alcohol of the alcohols used, in particular of types (II) and (III), into the distillation (D1) column, and a second entry line brings the remaining portions of the initial ester, or in particular the acetate (I), and of the mixture (M2) and all of the heaviest alcohol of the alcohols used, in particular of types (II) and (III), into the distillation (D1) column at a point that is higher in relation to that of the first entry line.

The process of the present invention can be carried out in devices such as those described diagrammatically in FIGS. 1 to 4.

Figure 1:
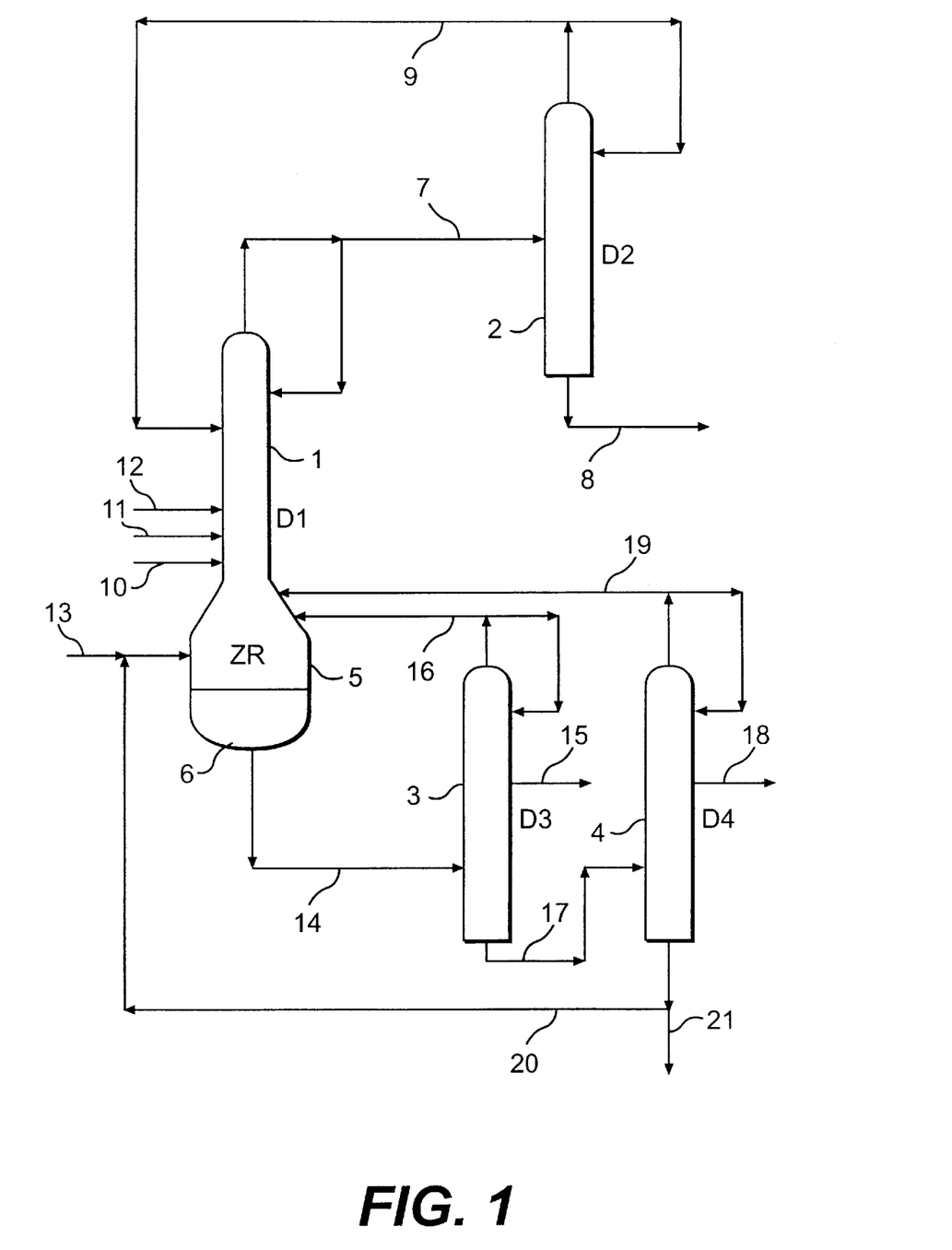
FIG. 1 shows diagrammatically a device capable of implementing the process of the invention, in particular in the case where two esters, or in particular acetates (IV) and (V), are manufactured continuously and simultaneously, this device including a reaction zone (RZ) carrying above it a distillation (D1) column, itself connected to a distillation (D2) column, separating in particular the alcohol formed (VI), and to a device of two successive distillation (D3) and (D4) columns where the esters manufactured, or in particular acetates (IV) and (V), are separated and isolated.

FIG. 1 shows diagrammatically a device enabling two esters, or in particular acetates (IV) and (V), to be manufactured continuously and simultaneously. The two simultaneous transesterification reactions are carried out in the reaction zone (RZ) which comprises a reactor (5) containing the reaction mixture (6) in homogeneous liquid phase, and which is surmounted by a distillation (D1) column (1). At the top of the column (1) comes out a conduit (7), where the azeotropic mixture (M1) circulates continuously and which is connected to a distillation (D2) column (2). At the bottom of the column (2) comes out a conduit (8), allowing the alcohol formed, in particular of type (VI) to be separated off and recovered. At the top of the column (2) comes out a conduit (9), where the new azeotropic mixture (M2) circulates continuously and which is connected to the column (1).

The feed conduits for fresh reactants, in particular the conduits (10), (11), (12), bringing, respectively, the initial ester, or in particular the acetate (I), and the alcohols used, in particular of types (II) and (III), emerge into the column (1).

A catalyst feed conduit (13) emerges into the reactor (5). At the bottom of the reaction zone (RZ) and of the distillation (D1) comes out a conduit (14), continuously feeding a distillation (D3) column (3), where the esters, or in particular the acetate which is the lightest of the esters manufactured, or in particular of the acetates of types (IV) and (V), is separated off via a conduit (15). At the top of the column (3), a mixture resulting from the distillation (D3) is continuously returned towards the reaction zone (RZ) via a conduit (16). At the bottom of the column (3) comes out a conduit (17), continuously feeding a distillation (D4) column (4), where the ester, or in particular the acetate which is the heaviest of the esters manufactured, or in particular of the acetates of types (IV) and (V), is separated off via a conduit (18). At the top of the column (4) comes out a conduit (19) continuously returning a mixture resulting from the distillation (D4) towards the reaction zone (RZ). At the bottom of the column (4) comes out a conduit (20) where a mixture containing a portion of the catalyst circulates, which is continuously and partly returned towards the reaction zone (RZ) via the conduit (13), the remaining portion of the said mixture being removed via a purge line (21).

Figure 2:
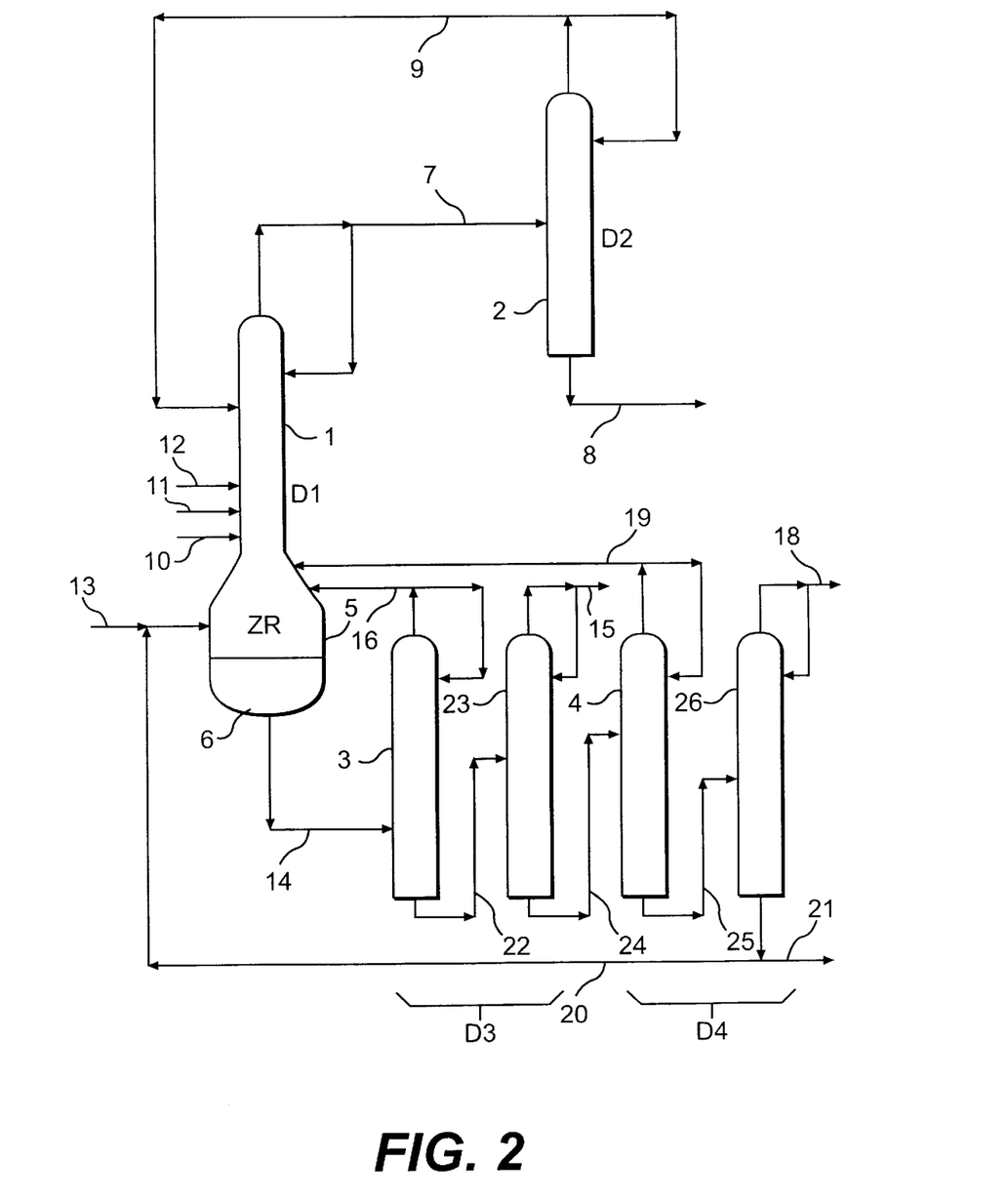
FIG. 2 shows diagrammatically an alternative form of the device described in FIG. 1, where each of the distillation (D3) and (D4) columns has been replaced by a set of two columns in series.

FIG. 2 shows diagrammatically a device that is identical with that shown in FIG. 1 and employing the same reference to mark the same components, except that the distillations (D3) and (D4) are carried out differently. The conduit (14) continuously feeds a distillation (D3) comprising two columns (3) and (23) arranged in series, a first column (3) to which the conduit (14) is connected and from which comes out at the bottom a conduit (22) which continuously feeds a second column (23). At the top of the column (3) comes out a conduit (16) which is connected to the reaction zone (RZ). At the top of the column (23), the ester, or in particular the acetate, which is the lightest of the esters manufactured, or in particular of the acetates of types (IV) and (V), is separated off via a conduit (15). At the bottom of the column (23) comes out a conduit (24) which connects and continuously feeds the distillation (D4) which comprises two columns (4) and (26) arranged in series, a first column (4), to which the conduit (24) is connected and from which comes out at the bottom a conduit (25) which continuously feeds a second column (26). At the top of the column (4) comes out a conduit (19) which is connected to the reaction zone (RZ). At the top of the column (26), the ester, or in particular the acetate, which is the heaviest of the esters manufactured, or in particular of the acetates of types (IV) and (V), is separated off via a conduit (18). At the bottom of the column (26) comes out a conduit (20) where a mixture containing a portion of the catalyst circulates, which is partly and continuously returned towards the reaction zone (RZ) via the conduit (13), the remaining part of the said mixture being removed via a purge line (21).

Figure 3:
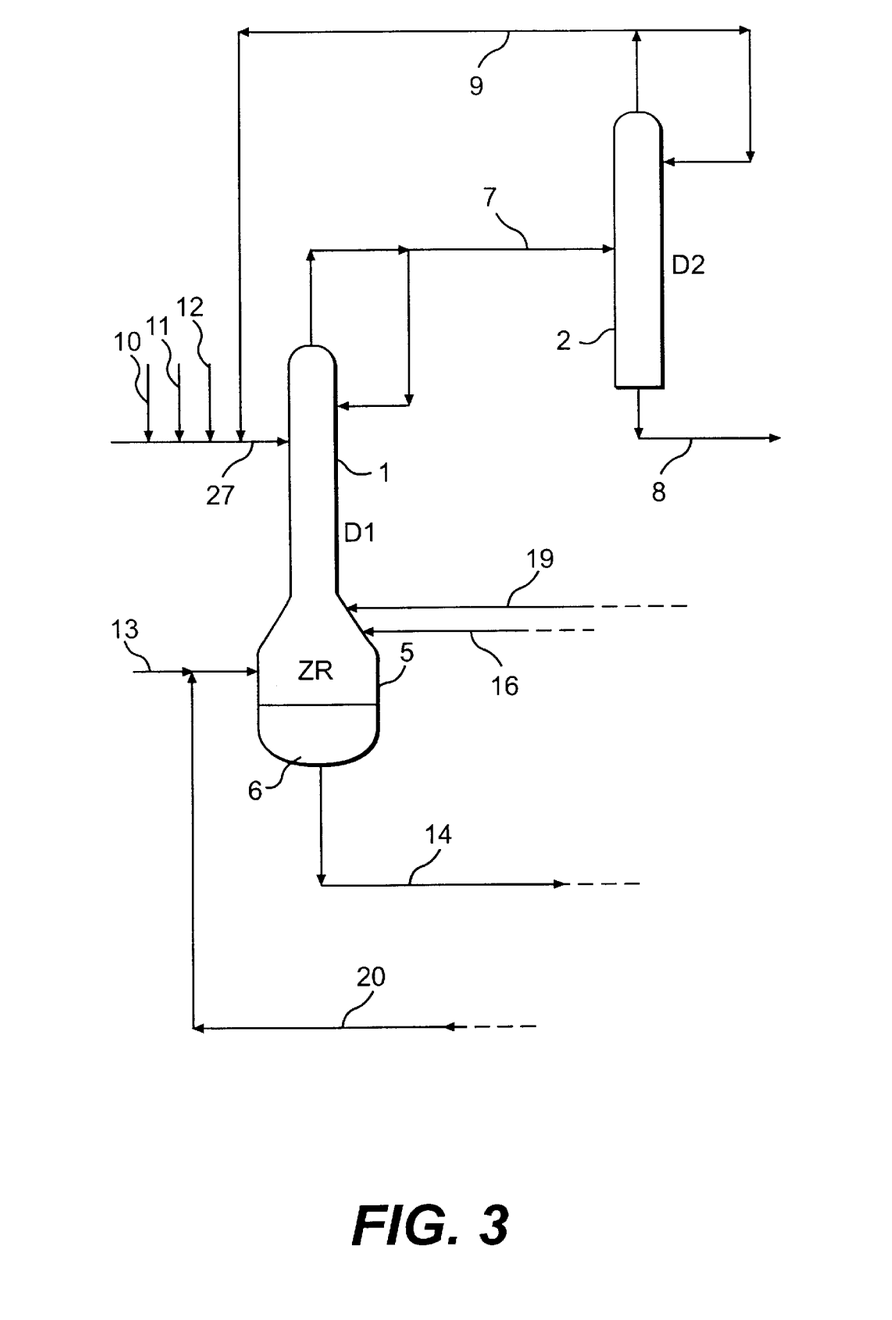
FIGS. 3 and 4 show diagrammatically two alternative forms of a portion of the device described in FIG. 1 or 2, including the reaction zone (RZ) and the distillation (D1) and (D2) columns, as well as, more precisely, the reactant feed of (RZ) and (D1).

FIG. 3 shows diagrammatically a portion of the devices shown in FIGS. 1 or 2, employing the same references to mark the same components, but with different devices for introducing the reactants into the distillation (D1). The conduits (10), (11) and (12) for feeding, respectively, initial ester, or in particular acetate (I), and alcohols used, in particular of types (II) and (III), emerge into a conduit (27) connected to the column (1). Into the conduit (27) also emerges the conduit (9), where the new azeotropic mixture (M2) originating from the distillation (D2) circulates continuously.

Figure 4:
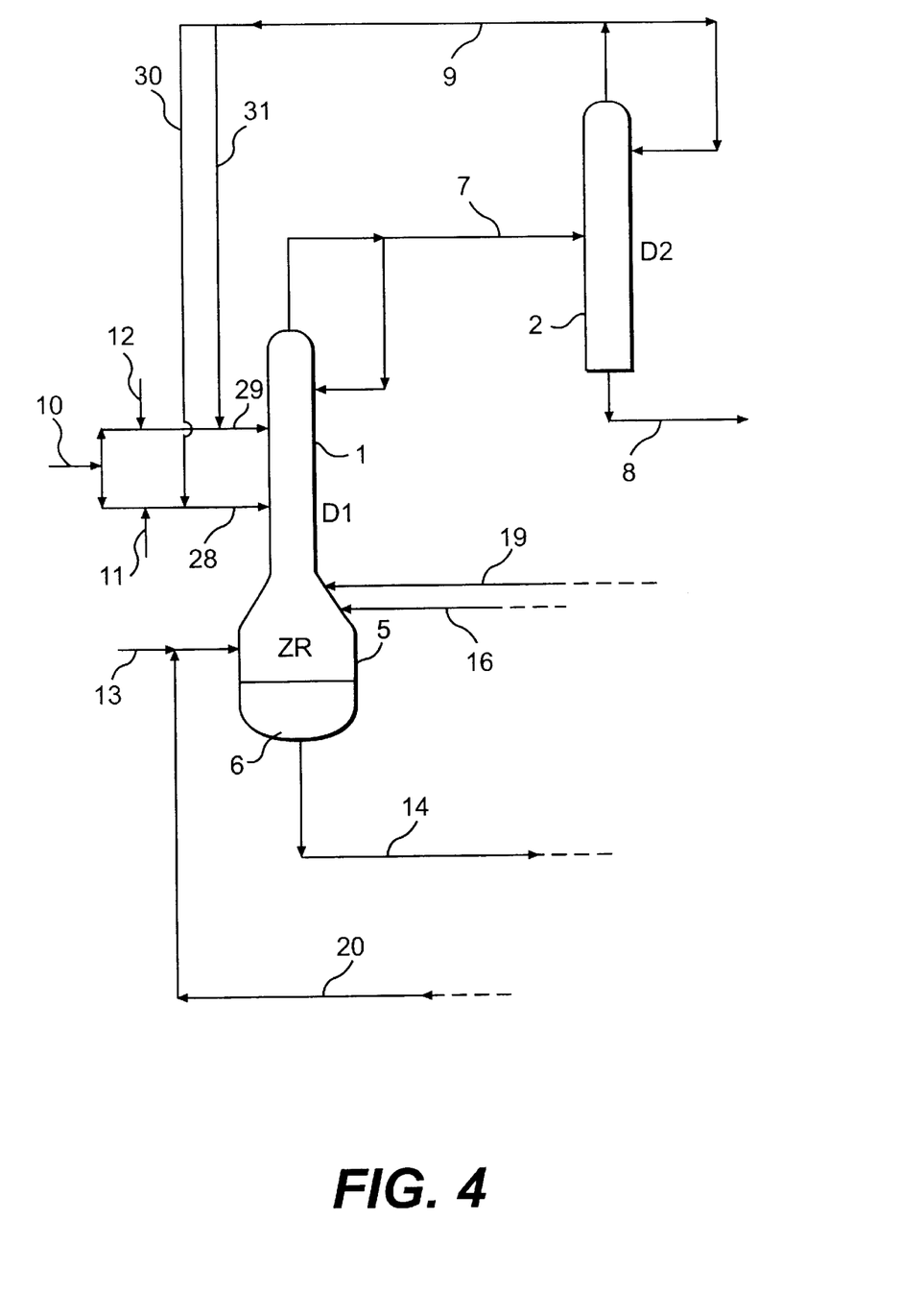

FIG. 4 shows diagrammatically a portion of the devices shown in FIGS. 1 or 2, employing the same references to mark the same components, but with different devices for introducing the reactants into the distillation (D1). The feed conduit (10) for initial ester, or in particular acetate (I), is divided into two conduits (28) and (29), each emerging into the column (1). The conduit (9) continuously returning the new azeotropic mixture (M2) from the distillation (D2) towards the distillation (D1) is divided into two conduits (30) and (31), each emerging into the conduits (28) and (29) respectively. Into the conduit (28) also emerges the conduit (11) for feeding the lightest alcohol of the alcohols used, in particular of types (II) and (III). Into the conduit (29) also emerges the conduit (12) for feeding the heaviest alcohol of the alcohols used, in particular of types (II) and (III).

The present invention is illustrated by the following examples.

EXAMPLE 1

The continuous and simultaneous manufacture of methoxypropanol acetate (MPA) and of monoethylene glycol butyl ether acetate (GBA) is carried out. Two simultaneous transesterification reactions are implemented by bringing ethyl acetate (EA) simultaneously into contact with methoxypropanol (MP) and monoethylene glycol butyl ether (GBE) according to the following equations:

The continuous and simultaneous manufacture of MPA and of GBA is carried out in a device as shown in FIG. 2. The ethyl acetate (EA), the methoxypropanol (MP) and the monoethylene glycol butyl ether (GBE) are introduced continuously and simultaneously into the reactor (5) at a temperature of 155° C. at an absolute pressure of 0.43 MPa, via the conduits (10), (11) and (12) respectively. The quantities of MP and of GBE which are introduced are in a molar ratio of MP to GBE of 1:0.28. The quantity of EA which is introduced is in a molar ratio of EA to the sum of the quantities of MP and GBE which are introduced of 1:1.

The simultaneous transesterification reactions are carried out in the presence of a catalyst consisting of tetraethyl titanate introduced via the conduit (13) into the reactor (5) in a quantity such that the molar ratio of the quantity of catalyst to the sum of the quantities of MP and of GBE is 0.005:1.

The reaction zone (RZ) includes a reactor (5) which is surmounted by a distillation (D1) column (1) including 21 theoretical plates. An azeotropic mixture (M1) consisting of ethanol and of ethyl acetate in an ethanol:EA weight ratio of 40:60 runs at 118° C. at the top of the column (1) into the conduit (7). The mixture (M1) continuously feeds a distillation (D2) column (2) including 30 theoretical plates and maintained at an absolute pressure of 0.03 MPa. The ethanol comes out at 51° C. at the bottom of the column (2). At the top of the column (2) a new azeotropic mixture (M2) consisting of ethanol and ethyl acetate in an ethanol:EA weight ratio of approximately 25:75 is recycled continuously via the conduit (9) into the column (1).

A mixture including in particular MPA and the GBA recovered at the bottom of the reactor (5) is conveyed continuously via a conduit (14) into a series of four columns (3), (23), (4) and (26) for distillations (D3) and (D4), in order to separate the MPA and the GBA continuously from this mixture. The mixture thus continuously feeds via the conduit (14) a distillation column (3) including 18 theoretical plates at an absolute pressure of 0.07 MPa. The unreacted MP and EA are recovered in particular at the top of the column (3) and are continuously recycled with the reactor (5) via the conduit (16). At the bottom of the column (3) is recovered a mixture which, via the conduit (22), continuously feeds a distillation column (23) including 15 theoretical plates at an absolute pressure of 0.04 MPa. The MPa is separated off at the top of the column (23) and is recovered continuously via the conduit (15). At the bottom of the column (23) a mixture is recovered which, via the conduit (24), continuously feeds a distillation column (4) including 15 theoretical plates at an absolute pressure of 0.04 MPa. The unreacted GBE is recovered in particular at the top of the column (4) and is continuously recycled towards the reactor (5) via the conduit (19). At the bottom of the column (4) is recovered a mixture which, via the conduit (25), continuously feeds a distillation column (26) including 10 theoretical plates at an absolute pressure of 0.04 MPa. The GBA is separated off at the top of the column (26) and is continuously recovered via the conduit (18). The catalyst is recovered in particular at the bottom of the column (26) and is continuously and partly recycled towards the reactor (5) via the conduit (20), the remaining part of this catalyst being removed to the outside via the purge (21).

MPA and GBA are thus manufactured continuously and simultaneously with degrees of purity which are higher than 99.5% by weight, in an MPA:GBA molar proportion which is substantially identical with the MP:GBE molar proportion used, that is to say 1:0.28.

EXAMPLE 2

The operation is carried out exactly as in Example 1, except for the fact that a device as shown in FIG. 1 is employed.

The mixture including in particular MPA and the GBA recovered at the bottom of the reactor (5) is continuously conveyed via a conduit (14) into a series of two columns (3) and (4) for distillations (D3) and (D4), in order to separate MPA and GBA continuously from this mixture. The mixture thus continuously feeds via the conduit (14) a distillation column (3) including 35 theoretical plates at an absolute pressure of 0.07 MPa. The MPA is separated off by the column (3) and is thus continuously recovered via the conduit (15). The unreacted MP and EA are recovered in particular at the top of the column (3) and are continuously recycled towards the reactor (5) via the conduit (16). At the bottom of the column (3) is recovered a mixture containing in particular GBA which continuously feeds via the conduit (17) a distillation column (4) including 30 theoretical plates at an absolute pressure of 0.04 MPa. GBA is separated off by the column (4) and is thus recovered continuously via the conduit (18). The unreacted GBE is recovered in particular at the top of the column (4) and is continuously recycled towards the reactor (5) via the conduit (19). The catalyst is recovered in particular at the bottom of the column (4) and is partly recycled continuously towards the reactor (5) via the conduit (20), the remaining part of this catalyst being removed to the outside via the purge (21).

The MPA and the GBA are thus obtained in purity conditions similar to those of Example 1 and in substantially identical molar proportions.

EXAMPLE 3

The operation is carried out exactly as in Example 1, except for the fact that the quantities of MP and of GBE which are introduced are in a molar ratio of MP to GBE not of 1:0.28 but of 1:1.

MPA and GBA are thus manufactured continuously and simultaneously with degrees of purity which are identical with those obtained in Example 1 and in an MPA:GBA molar proportion which is substantially identical with that of MP:GBE used, that is to say 1:1.

EXAMPLE 4

Continuous and simultaneous manufacture of ethoxypropanol acetate (EPA) and of diethylene glycol butyl ether acetate (DGBA) is carried out. Two simultaneous transesterification reactions are implemented by bringing ethyl acetate (EA) simultaneously into contact with ethoxypropanol (EP) and diethylene glycol butyl ether (DGBE) according to the following equations:

The continuous and simultaneous manufacture of EPA and of DGBA is carried out in a device as shown in FIG. 2. The ethyl acetate (EA), ethoxypropanol (EP) and diethylene glycol butyl ether (DGBE) are introduced simultaneously and continuously into the reactor (5) at a temperature of 164° C. at an absolute pressure of 0.43 MPa, via the conduits (10), (11) and (12) respectively. The quantities of EP and of DGBE which are introduced are in a molar ratio of EP to DGBE of 1:1. The quantity of EA which is introduced is in a molar ratio of 1:1 of EA to the sum of the quantities of EP and of DGBE which are introduced.

The simultaneous transesterification reactions are carried out in the presence of a catalyst consisting of tetraethyl titanate introduced via the conduit (13) into the reactor (5) in a quantity such that the molar ratio of the quantity of catalyst to the sum of the quantities of EP and of DGBE is 0.006:1

The reaction zone (RZ) includes a reactor (5) which is surmounted by a distillation (D1) column (1) including 21 theoretical plates. An azeotropic mixture (M1) consisting of ethanol and ethyl acetate in an ethanol:EA weight ratio of 40:60 runs at 118° C. at the top of the column (1) into the conduit (7). The mixture (M1) continuously feeds a distillation (D2) column (2) including 30 theoretical plates and maintained at an absolute pressure of 0.03 MPa. The ethanol comes out at 51° C. at the bottom of the column (2). At the top of the column (2) a new azeotropic mixture (M2) consisting of ethanol and of ethyl acetate in a ethanol:EA weight ratio of approximately 25:75 is continuously recycled via the conduit (9) into the column (1).

A mixture including in particular EPA and the DGBA recovered at the bottom of the reactor (5) is continuously conveyed via a conduit (14) into a series of four columns (3), (23), (4) and (26) for distillations (D3) and (D4), in order to separate the EPA and DGBA continuously from this mixture. The mixture thus continuously feeds via the conduit (14) a distillation column (3) including 18 theoretical plates at an absolute pressure of 0.07 MPa. The unreacted EP and EA are recovered in particular at the top of the column (3) and are continuously recycled towards the reactor (5) via the conduit (16). At the bottom of the column (3) is recovered a mixture which, via the conduit (22), continuously feeds a distillation column (23) including 15 theoretical plates at an absolute pressure of 0.04 MPa. The EPA is separated off at the top of the column (23) and is continuously recovered via the conduit (15). At the bottom of the column (23) is recovered a mixture which, via the conduit (25), continuously feeds a distillation column (4) including 15 theoretical plates at an absolute pressure of 0.04 MPa. The unreacted DGBE is recovered in particular at the top of the column (4) and is continuously recycled towards the reactor (5) via the conduit (19). At the bottom of the column (4) is recovered a mixture which, via the conduit (25), continuously feeds a distillation column (26) including 10 theoretical plates at an absolute pressure of 0.04 MPa. The DGBA is separated off at the top of the column (26) and is continuously recovered via the conduit (18). The catalyst is recovered in particular at the bottom of the column (26) and is continuously and partly recycled towards the reactor (5) via the conduit (20), the remaining part of this catalyst being removed to the outside via the purge (21).

EPA and DGBA are thus manufactured continuously and simultaneously with degrees of purity which are higher than 98% by weight, in an EPA:DGBA molar proportion which is substantially identical to the EP:DGBE molar proportion used, that is to say 1:1.

What is claimed is:

1. A process for the continuous and simultaneous manufacture of at least two different acetates by at least two simultaneous transesterification reactions comprising continuously bringing into contact in the presence of a catalyst in a reaction zone:

(i) an acetate of the formula $$CH_3COOR \quad (I)$$

in which R is an alkyl radical, with (ii) at least two alcohols of formulae $$R^1OH \quad (II)$$

and $$R^2OH \quad (III)$$

in which $R^1$ and $R^2$, are different, and are alkyl radicals with a linear or branched chain, or radicals of formula $$R^3(OCH_2CR^4R^5)_m—$$

in which $R^3$ is an alkyl radical, $R^4$ and $R^5$, being identical or different, are a hydrogen atom or an alkyl radical, and m is an integer of from 1 to 4
to form a reaction mixture having a homogeneous liquid phase and produce in the reaction zone by at least two simultaneous transesterification reactions of (i) with (ii) at least two acetates of formulae $$CH_3COOR^1 \quad (IV)$$

and $$CH_3COOR^2 \quad (V)$$

and continuously drawing off from said reaction zone said at least two acetates (IV) and (V) and continuously separating said at least two acetates (IV) and (V) from each other by at least twice successively distilling the reaction mixture present in the reaction zone.

2. The process of claim 1, wherein the products resulting from these reactions include the at least two acetates (IV) and (V) and an alcohol of formula $$ROH \quad (VI)$$

in which R is the alkyl radical, the components (i) and (ii) brought into contact in the reaction zone forming a reaction mixture with the products resulting from these reactions and wherein the step of continuously separating said at least two acetates (IV) and (V) from each other includes the steps of (a) continuously distilling the reaction mixture at a pressure which is substantially identical with a pressure existing in the reaction zone and continuously separating a light fraction containing at least one azeotropic mixture (MI) formed of the acetate (I) and the alcohol (VI) from a heavy fraction containing the at least two acetates (IV) and (V), (b) continuously distilling the light fraction at a pressure which differs from that existing in (a), so as to separate off continuously a portion of the alcohol (VI), and (c) successively and continuously distilling at least twice the heavy fraction, so as to separate off continuously the at least two acetates (IV) and (V).

3. The process of claim 1 or 2, wherein R is a $C_1$–$C_4$ alkyl radical.

4. The process of claim 1 or 2, wherein $R^1$ and $R^2$ are $C_4$–$C_{12}$ alkyl radicals, or radicals of formula $$R^3(OCH_2CR^4R^5)_m—$$

in which $R^3$ is a $C_1$–$C_6$ alkyl radical $C_1$–$C_4$, $R^4$ and $R^5$, being identical or different, are a hydrogen atom or $C_1$–$C_4$ alkyl radical, and m is an integer of from 1 or 2.

5. The process of claim 1 or 2, wherein of said at least two alcohols (II) and (III), one is a primary or secondary alcohol and the other is a secondary or tertiary alcohol.

6. The process of claim 1, wherein said at least two alcohols (II) and (III) are mono- or polyalkylene glycol ethers of formula $$R^3(OCH_2CR^4R^5)_mOH \quad (VII)$$

in which $R^3$ is an alkyl radical, $R^4$ and $R^5$, being identical or different are a hydrogen atom or a $C_1$–$C_4$ alkyl radical, and m is an integer of from 1 to 4.

7. The process of claim 1, wherein of said at least two alcohols (II) and (III), one is a mono- or polyethylene glycol ether of formula $$R^3(OCH_2CH_2)_mOH \quad (VIII)$$

and the other is mono- or polypropylene glycol ether of formula $$R^3(OCH_2CHCH_3)_mOH \quad (IX)$$

in which $R^3$ is an alkyl radical and m is an integer ranging of from 1 to 4.

8. The process of claim 6 or 7, wherein $R^3$ is a $C_1$–$C_6$ alkyl radical and m is an integer of from 1 or 2.

9. The process of claim 1 or 2, wherein the at least two alcohols have boiling points at atmospheric pressure whose difference is from 10 to 60° C.

10. The process of claims 1 or 2, wherein the catalyst is a metal alcoholate, the metal of the alcoholate belonging to groups I to IV of the Periodic Classification of the elements.

11. The process of claim 2, wherein the distillation in step (b), is carried out at a pressure lower than that existing in the reaction zone and in step (a).

12. The process of claim 2 or 11, wherein during distillation in step (b), a proportion of the alcohol (VI) is separated off and an azeotropic mixture (M2) is formed of the acetate (I) and the alcohol (VI) in a content that is lower than that of alcohol (VI) of the azeotropic mixture (MI), the azeotropic mixture (M2) being at least partly returned continuously into the reaction zone and/or into the distillation in step (a).

13. The process of claim 2 or 11, wherein the heavy fraction from step (a) is continuously subjected to a first distillation in step (c) where the lightest acetate of the at least two acetates (IV) and (V) is separated off, a top fraction therefrom being at least partly returned continuously into the reaction zone and/or into the distillation in step (a) and a tail fraction therefrom being continuously fed to a second distillation in step (c) where the heaviest acetate of the at least two acetates (IV) and (V) is separated off, a top and a tail fraction therefrom being at least partly returned continuously into the reaction zone and/or into the distillation step (a).

* * * * *